US011472898B2

(12) United States Patent
Wang et al.

(10) Patent No.: US 11,472,898 B2
(45) Date of Patent: Oct. 18, 2022

(54) METHOD FOR SURFACE MODIFICATION OF NANOPARTICLES

(71) Applicant: City University of Hong Kong, Kowloon (HK)

(72) Inventors: Feng Wang, New Territories (HK); Wei Kong, Sheung Wan (HK); Tianying Sun, Kowloon Tong (HK)

(73) Assignee: City University of Hong Kong, Kowloon (HK)

( * ) Notice: Subject to any disclaimer, the term of this patent is extended or adjusted under 35 U.S.C. 154(b) by 538 days.

(21) Appl. No.: 15/410,849

(22) Filed: Jan. 20, 2017

(65) Prior Publication Data

US 2018/0208688 A1 Jul. 26, 2018

(51) Int. Cl.

| | |
|---|---|
| ***C08F 120/08*** | (2006.01) |
| ***G01N 33/58*** | (2006.01) |
| ***C08F 120/06*** | (2006.01) |
| *B82Y 40/00* | (2011.01) |

(52) U.S. Cl.

CPC ......... *C08F 120/06* (2013.01); *G01N 33/587* (2013.01); *B82Y 40/00* (2013.01); *Y10S 977/773* (2013.01); *Y10S 977/896* (2013.01); *Y10S 977/904* (2013.01); *Y10S 977/948* (2013.01)

(58) Field of Classification Search

None

See application file for complete search history.

(56) References Cited

FOREIGN PATENT DOCUMENTS

CN 103773359 A 5/2014

OTHER PUBLICATIONS

Wen et al., (Nanocrystalline Materials (Second Edition. pp. 121-160. 2014) Lanthanide-Doped Nanoparticles: . . . .*

Zhano et al. (Nano Letters. 7(10) 3203-3207, 2007) A General Approach for Transferring . . . .*

Naccache et al. (Chem. Mater., 21, 717-723, 2009) Controlled Synthesis and Water Dispersibility of Hexagonal Phase . . . .*

Q. Liu, W. Feng, T. S. Yang and F. Y. Li, "Upconversion luminescence imaging of cells and small animals", Nature Protocols, vol. 8, No. 10, pp. 2033-2044, 2013.

J. J. Peng, W. Xu, C. L. Teoh, S. Y. Han, B. Kim, A. Samanta, J. C. Er, L. Wang, L. Yuan, X. G. Liu and Y. T. Chang, "High-efficiency in vitro and in vivo detection of Zn2+ by dye-assembled upconversion nanoparticles", Journal of the American Chemical Society, pp. 1-9, 2015.

Z. W. Wei, L. N. Sun, J. L. Liu, J. Z. Zhang, H. R. Yang and Y. Yang, "Cysteine modified rare-earth up-converting nanoparticles for in vitro and in vivo bioimaging", Z. Wei et al / Biomaterials, vol. 35, pp. 387-392, 2014.

A. G. Dong, X. C. Ye, J. Chen, Y. J. Kang, T. Gordon, J. M. Kikkawa and C. B. Murray, "A generalized ligand-exchange strategy enabling sequential surface functionalization of colloidal nanocrystals", Journal of the American Chemical Society, vol. 133, pp. 998-1006, 2011.

* cited by examiner

*Primary Examiner* — Tigabu Kassa

(74) *Attorney, Agent, or Firm* — Renner Kenner Greive Bobak Taylor & Weber

(57) ABSTRACT

A method for surface modification of nanoparticles includes the separate steps of removing ligands from the surface of the nanoparticles to form ligand-free nanoparticles, and mixing new ligands with the ligand-free nanoparticles to form modified nanoparticles.

12 Claims, 7 Drawing Sheets

METHOD FOR SURFACE MODIFICATION OF NANOPARTICLES

FIELD OF INVENTION

The invention relates to a method for surface modification of nanoparticles.

BACKGROUND

Nanoparticles are particles between 1 and 100 nanometres in size. Properties of these ultrafine particles are typically characterized by the components on their surfaces due to large surface area-to-volume ratios, which often enable high reactivity. As such, multiple uses have been found for nanoparticles, particularly in optical and medical fields of technology.

Lanthanide-doped nanoparticles comprise nanocrystals of a transparent material such as $NaYF_4$ doped with lanthanide ions, which has unique optical properties in that near-infrared light can be used to produce visible light therefrom. This occurs via the process of photon upconversion, in which the sequential absorption of two or more photons leads to the emission of light at shorter wavelength than the excitation wavelength.

One of the most common lanthanide ions used in photon upconversion is the pair erbium-ytterbium ($Er^{3+}$, $Yb^{3+}$), whereby ytterbium ions are provided as antennas to absorb light at around 980 nm and transfer it to the upconverter erbium ions, which emit a characteristic green and red light.

As-synthesized Upconverting Nanoparticles (UCNPs) are usually capped with organic ligands that aid in size and shape control during preparation. However, as these ligands make the nanoparticles' surface hydrophobic they are not dispersible in aqueous solution, which prevents biological applications.

One simple method to increase solubility in aqueous solvents is direct ligand exchange. This requires a more favoured ligand to replace the initial ones. The hydrophobic native ligand capping the nanoparticle during synthesis (usually a long chain molecule like oleic acid) is directly substituted with a more polar hydrophilic one, which is usually multi chelating (e.g. poly(ethyleneglycol) (PEG)-phosphate, poly(acrylic acid)) and hence provides better stabilisation/binding resulting in their exchange.

The protocol for direct exchange is simple, generally involving mixing for an extended period of time. However, the work-up can be tedious, conditions must be optimized for each system, and aggregation may occur. Another shortcoming is the slow kinetics associated with the exchange.

An aim of the invention therefore is to provide a method for surface modification of nanoparticles which overcomes the above issues.

SUMMARY OF INVENTION

In an aspect of the invention, there is provided a method for surface modification of nanoparticles comprising the steps of:

(a) removing ligands from the surface of the nanoparticles to form ligand-free nanoparticles;

(b) mixing new ligands with the ligand-free nanoparticles to form preliminary modified nanoparticles;

(c) solvotreating the preliminary modified nanoparticles to form modified nanoparticles;

characterised in that steps (a) and (b) are separate.

Advantageously by using the strategy where the ligand removal and addition steps are separate, the passive ligands were removed effectively and the abundant new ligands were coated more conveniently compared to existing methods.

In one embodiment the preliminary modified nanoparticles comprise weakly absorbed new ligands which are converted by the solvotreating step to firmly bonded new ligands on the modified nanoparticles.

In one embodiment the nanoparticles are doped with lanthanide. However, it will be appreciated that the method can be Applied to other kinds of ligands and nanoparticles, such as metal nanoparticles, metal oxide nanoparticles, and semiconductor nanoparticles.

In one embodiment the nanoparticles are coated with oleate ligands, or oleate and oleylamine ligands.

In one embodiment a hydrochloric acid solution is used to remove the oleate surfactant and form ligand-free nanoparticles. Typically the hydrochloric acid solution has a concentration of about 0.1M.

In one embodiment a new ligands solution is adjusted to pH8. Typically a sodium hydroxide solution is used to adjust the pH. Typically the pH is adjusted prior to reaction with the ligand-free nanoparticles. Most ligands solutions are acidic (except PEI solution which is pH 11.8).

In one embodiment the new ligands are provided in excess compared to the ligand-free nanoparticles. As such the amount of new ligands which may be bound is maximised as there are more new ligands than binding sites therefor.

In one embodiment the new ligands comprise any of poly(acrylic acid) (PAA), polyethylenimine (PEI), polyvinylpyrrolidone (PVP), cysteine, glycine, citric acid, biotin, aminoethylphosphate (AEP), and/or the like.

In one embodiment the mixture of new ligands solution and the ligand-free nanoparticles are stirred for at least two hours.

In one embodiment water is substantially removed from the mixture, typically by dehydration.

In one embodiment diethylene glycol is added as a solvothermal solvent for use in solvothermal treatment.

In one embodiment the solvothermal treatment comprises heating the solution in an autoclave for at least two hours.

In one embodiment the solvothermal treatment comprises maintaining a temperature gradient ranging from 160° C. to 200° C. to minimise ligand degradation.

In one embodiment the resulting solution is centrifuged and the supernatant diethylene glycol is removed. Typically the pellet of nanoparticles is washed with a mixture of water and ethanol. Due to the density differences, the ligands modified nanoparticles will be precipitated during the centrifugation, while the unreacted ligands and diethylene glycol will still stay in solution. Washing removes both unreacted ligands and diethylene glycol to purify the nanoparticles.

In a further aspect of the invention there are provided modified nanoparticles made according to the method described herein.

BRIEF DESCRIPTION OF DRAWINGS

It will be convenient to further describe the present invention with respect to the accompanying drawings that illustrate possible arrangements of the invention. Other arrangements of the invention are possible, and consequently the particularity of the accompanying drawings is not to be understood as superseding the generality of the preceding description of the invention.

FIG. 3(*a*) FTIR spectra of upconversion nanoparticles coated with different types of ligands; FIG. 3(*b*) TEM images of upconversion nanoparticles coated with different types of ligands; FIG. 3(*c*) Photographs of upconversion nanoparticles coated with different types of ligands in water dispersion; FIG. 3(*d*) Viability of human lung adenocarcinoma cell incubated with different concentrations of surface-modified upconversion nanoparticles for 48 hr (in FIG. 3(*d*), the bar graphs at 4, 20, 100, and 500 μg/mL are positioned in the order as shown in the legend above the bar graphs).

DETAILED DESCRIPTION

Figure 1:
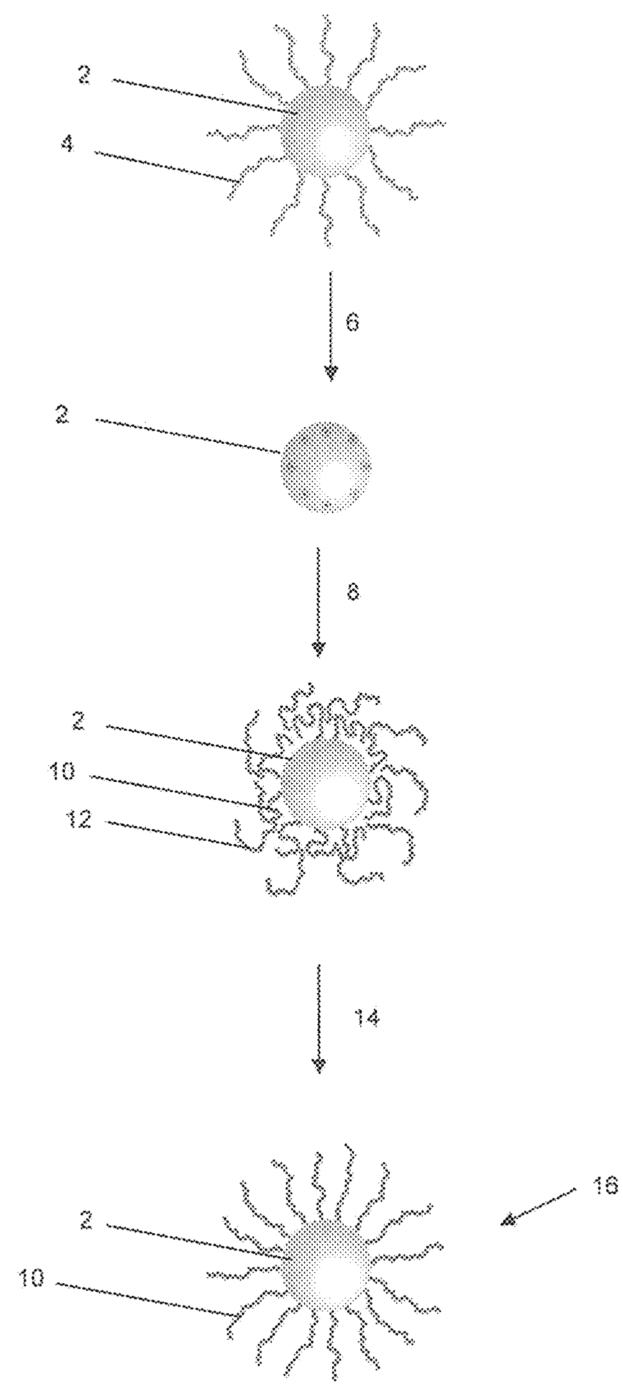
FIG. 1 is a schematic experimental design for surface modification of lanthanide-doped nanoparticles with various ligands according to an embodiment of the invention.

With regard to FIG. 1, a schematic diagram of the experimental design is illustrated, whereby in the first step 6 nanoparticles 2 coated with oleate ligands 4 are treated with 0.1M hydrochloric acid to remove the oleate ligands from the surface of the nanoparticles. For example, if the amount of rare earth elements used is 0.4 mmol, 4 mL of 0.1M hydrochloric acid will be needed to remove the oleate ligands.

In the next step 8 sodium hydroxide is used to adjust a solution of new ligands to pH 8, which is then mixed with the ligand-free nanoparticles for at least two hours, to form firmly bonded new ligands 10 and weakly absorbed new ligands 12 with the nanoparticles 2, referred to herein as preliminary modified nanoparticles.

The amount of ligand solution required depends on the ligand, but is generally provided such that the number of new ligands exceed the binding sites therefor. For example, for cysteine, glycine, citric acid and aminoethylphosphate, 100 mg of ligands is needed in modifying 0.5 mL of ligand-free nanoparticles. While for the other ligands such as poly(acrylic acid), polyethylenimine, polyvinylpyrrolidone, and biotin, 50 mg is needed.

The solution is then dehydrated by mixing the solution with diethylene glycol in a 50 mL ground flask, which is then heated at around 105° C. to remove the water. Diethylene glycol is used as a solvothermal solvent in solvothermal treatment 14, which converts the weakly absorbed new ligands on the preliminary modified nanoparticles to firmly bonded new ligands, thereby forming modified nanoparticles.

In solvothermal treatment the solution is heated in an autoclave for at least two hours. A temperature gradient ranging from 160° C. to 200° C. is maintained to minimise ligand degradation.

The resulting solution is then centrifuged, the supernatant diethylene glycol is removed, and the pellet of nanoparticles is washed with a mixture of water and ethanol. Due to the density differences, the ligands modified nanoparticles will be precipitated during the centrifugation, while the unreacted ligands and diethylene glycol will still stay in solution. Washing removes both unreacted ligands and diethylene glycol to purify the nanoparticles.

The separate steps of removing the native hydrophobic ligands and immobilization of new hydrophilic ligands results in modified nanoparticles 16 which display good water dispersibility, high colloidal stability, and good biocompatibility.

This technique can be used for ligand exchange of oleate-stabilized nanoparticles. The unreactive hydrophobic nanoparticles can be modified with a large variety of new ligands, which make them hydrophilic and suitable for bio-applications or further conjugation with other functional molecules. Furthermore, the technique can be readily extended to other ligand and nanoparticle systems for applications ranging from biological imaging to lighting and solar cells.

Figure 2:
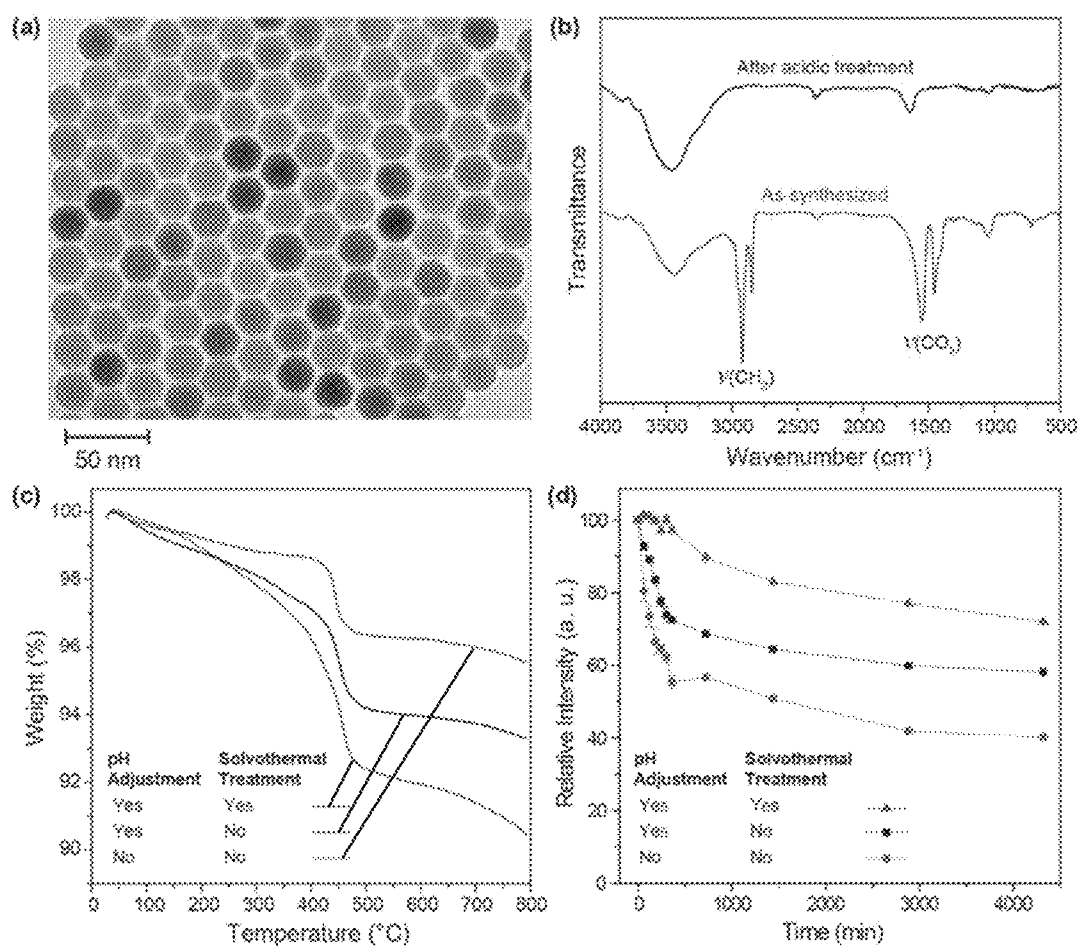
FIG. 2 illustrates various characteristics of the nanoparticles: (a) Typical TEM image of the as-synthesized NaYF4:Yb/Er@NaYF4 nanoparticles; (b) FTIR spectra of the upconversion nanoparticles before and after removal of oleate ligands; (c) Thermogravimetric curves of PAA-coated nanoparticles prepared under different experimental conditions. (d) Dispersion stability of PAA-coated nanoparticles prepared under different experimental conditions.
Figure 3A:
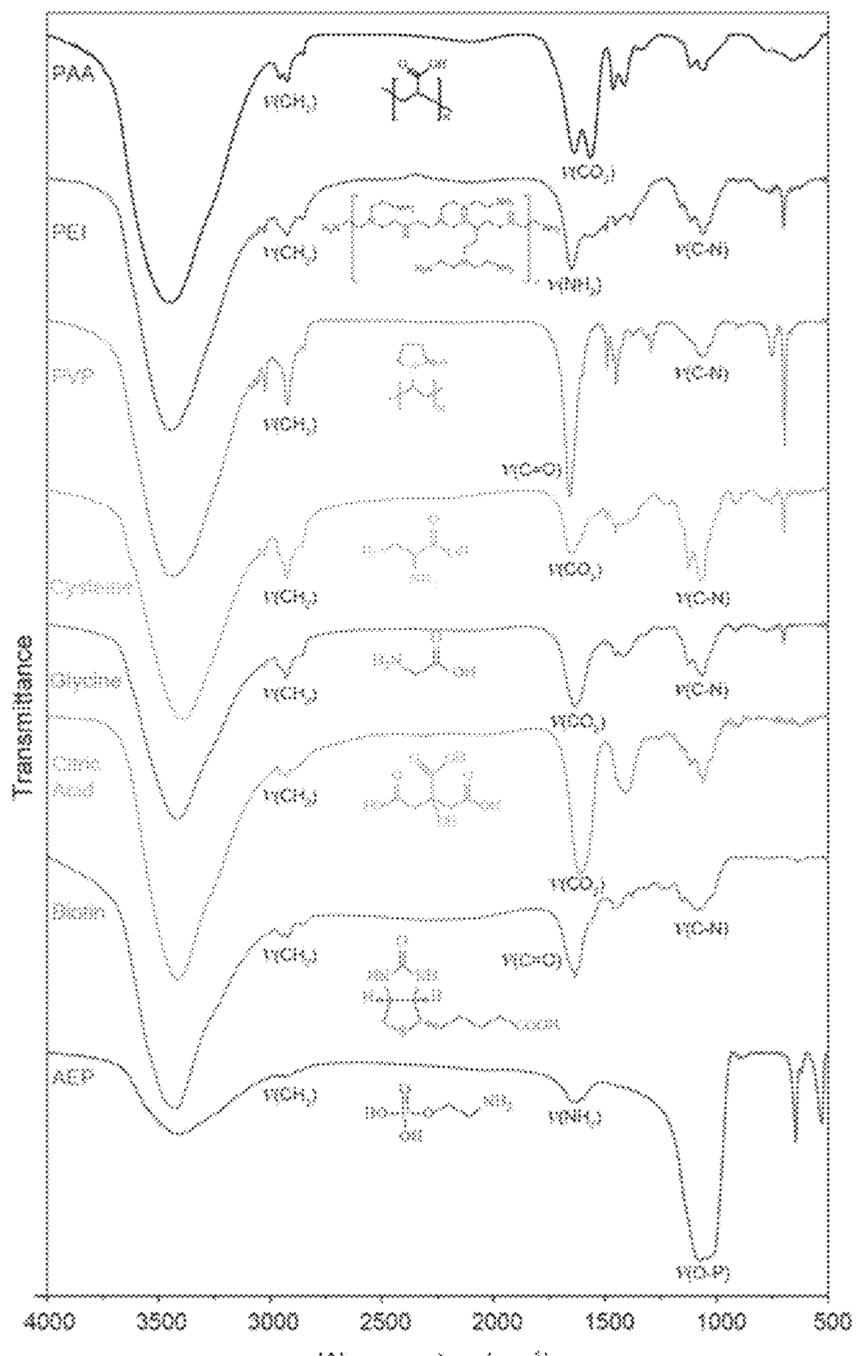
FIGS. 3(*a*), 3(*b*), 3(*c*) and 3(*d*) illustrate various characteristics of the upconverted nanoparticles.
Figure 3B:
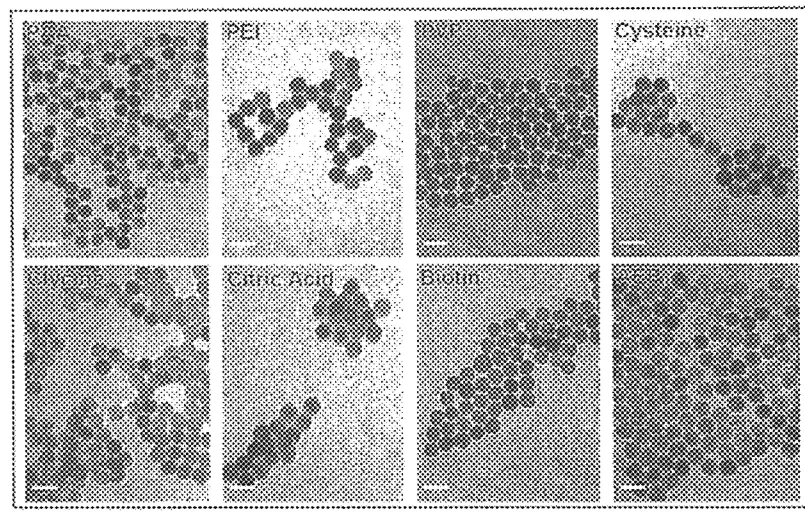
Figure 3C:
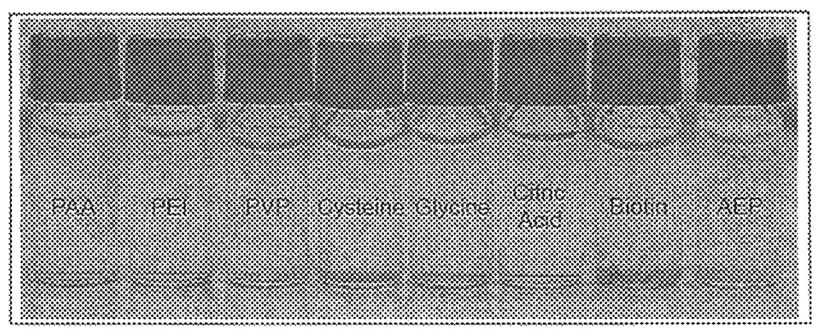
Figure 3D:
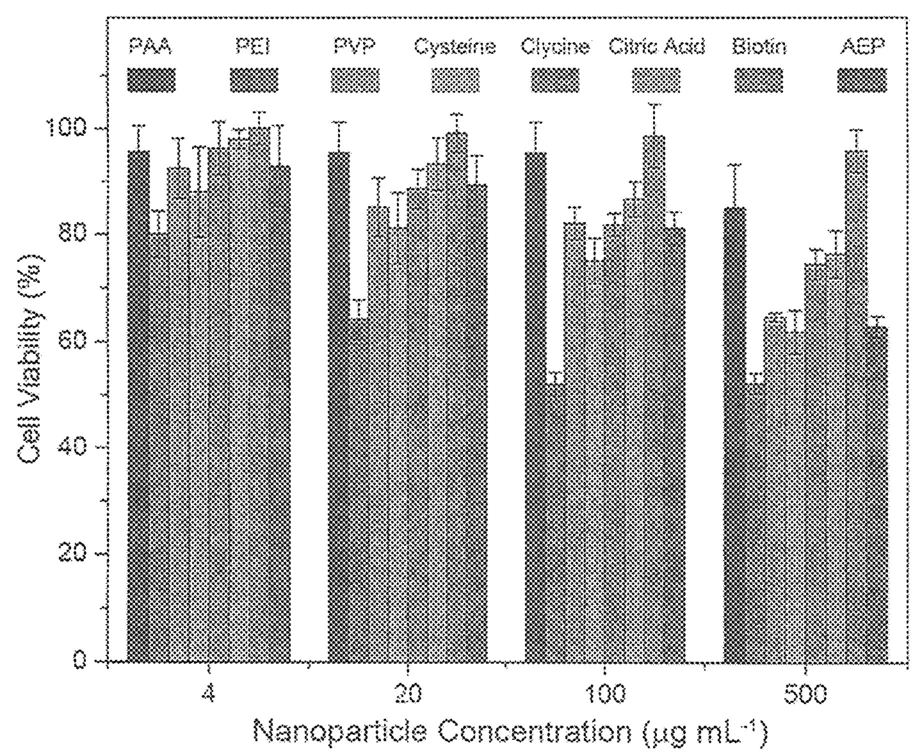

FIG. 2*a* illustrates a typical TEM image of the as-synthesized $NaYF_4$:Yb/Er@$NaYF_4$ nanoparticles whereas FIG. 2*b* illustrates FTIR spectra of the upconversion nanoparticles before and after removal of oleate ligands.

The nanoparticles may be coated with poly(acrylic acid) (PAA) and FIGS. 2*c-d* respectively illustrate thermogravimetric curves (TG) and dispersion stability of PAA-coated nanoparticles prepared under different experimental conditions to determine the effects of pH adjustment and solvothermal treatment. The intensities were obtained by recording the emission at 543 nm from aqueous dispersions of the nanoparticles (12.5 mM). The solid lines are intended to guide the eye. Error bars represent the standard deviations from 3 sets of repeated measurements. FIG. 2*c* indicates that more amount of PAA is modified on the surface of nanoparticles with both pH adjustment and solvothermal treatment. FIG. 2*d* indicates that the PAA modified nanoparticles will be more stable with both pH adjustment and solvothermal treatment.

FIGS. 3(*a*) through 3(*d*) illustrate various characteristics of the upconversion nanoparticles: FIG. 3(*a*) FTIR spectra of upconversion nanoparticles coated with different types of ligands which shows the characteristic peak of each ligand indicating the successful modification with the same; FIG. 3(*b*) TEM images of upconversion nanoparticles coated with different types of ligands which indicate the good dispersibility of the ligand-modified nanoparticles. Scale bars are 50 nm; FIG. 3(*c*) Photographs of upconversion nanoparticles coated with different types of ligands in water dispersions (12.5 mM) which also indicate the good dispersibility of the ligand-modified nanoparticles; FIG. 3(*d*) Viability of human lung adenocarcinoma cell incubated with different concentrations of surface-modified upconversion nanoparticles for 48 hr, which show the good biocompatibility of the ligand-modified nanoparticles (in FIG. 3(*d*), the bar graphs at 4, 20, 100, and 500 μg/mL are positioned in the order as shown in the legend above the bar graphs).

Figure 4:
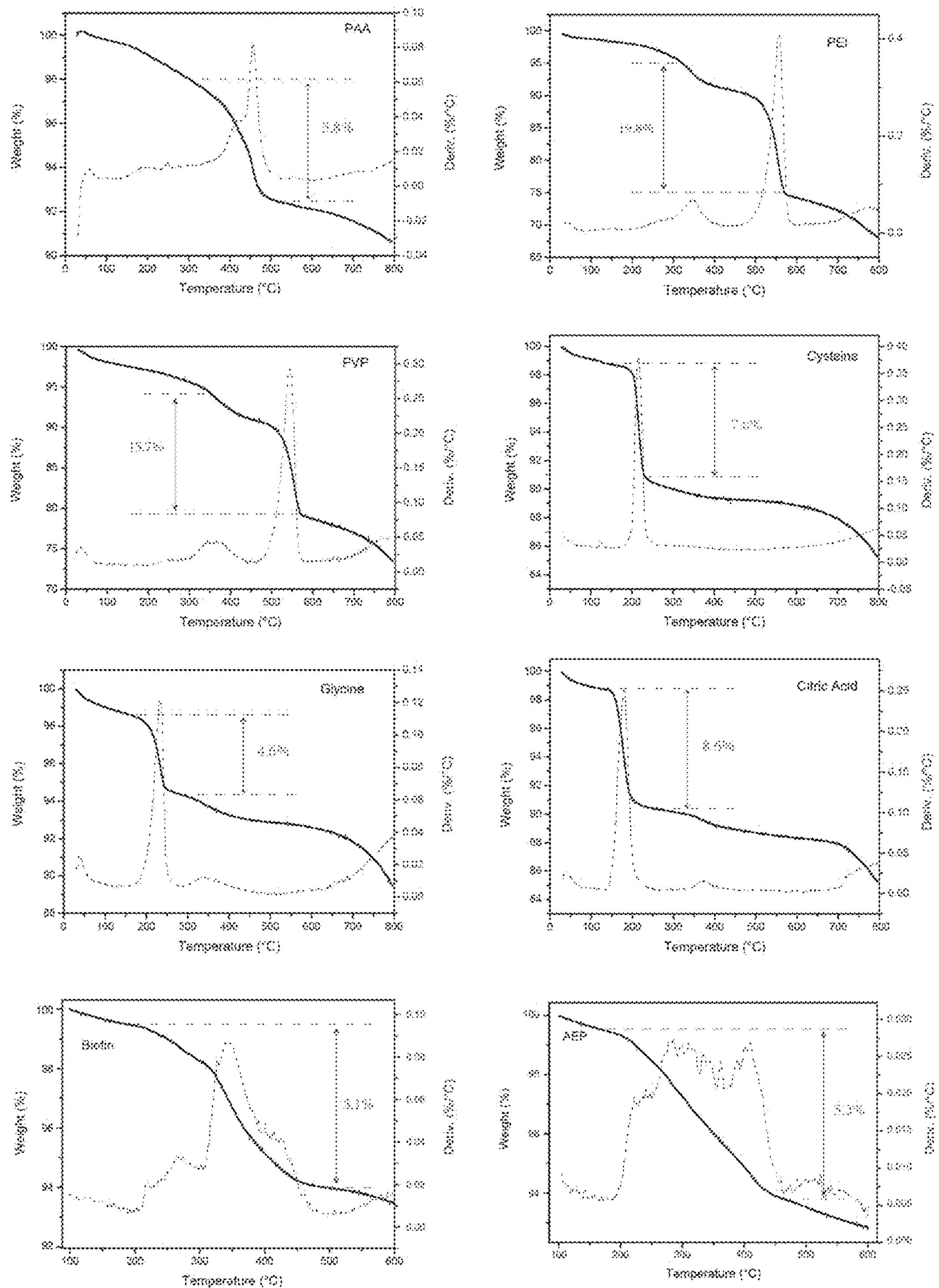
FIG. 4 illustrates thermogravimetric curves for upconversion nanoparticles modified with different types of ligands.

FIG. 4 illustrates thermogravimetric curves for upconversion nanoparticles modified with different types of ligands, wherein the weight loss in the curves indicates the amount of ligands modified on the surface of nanoparticles.

Figure 5:
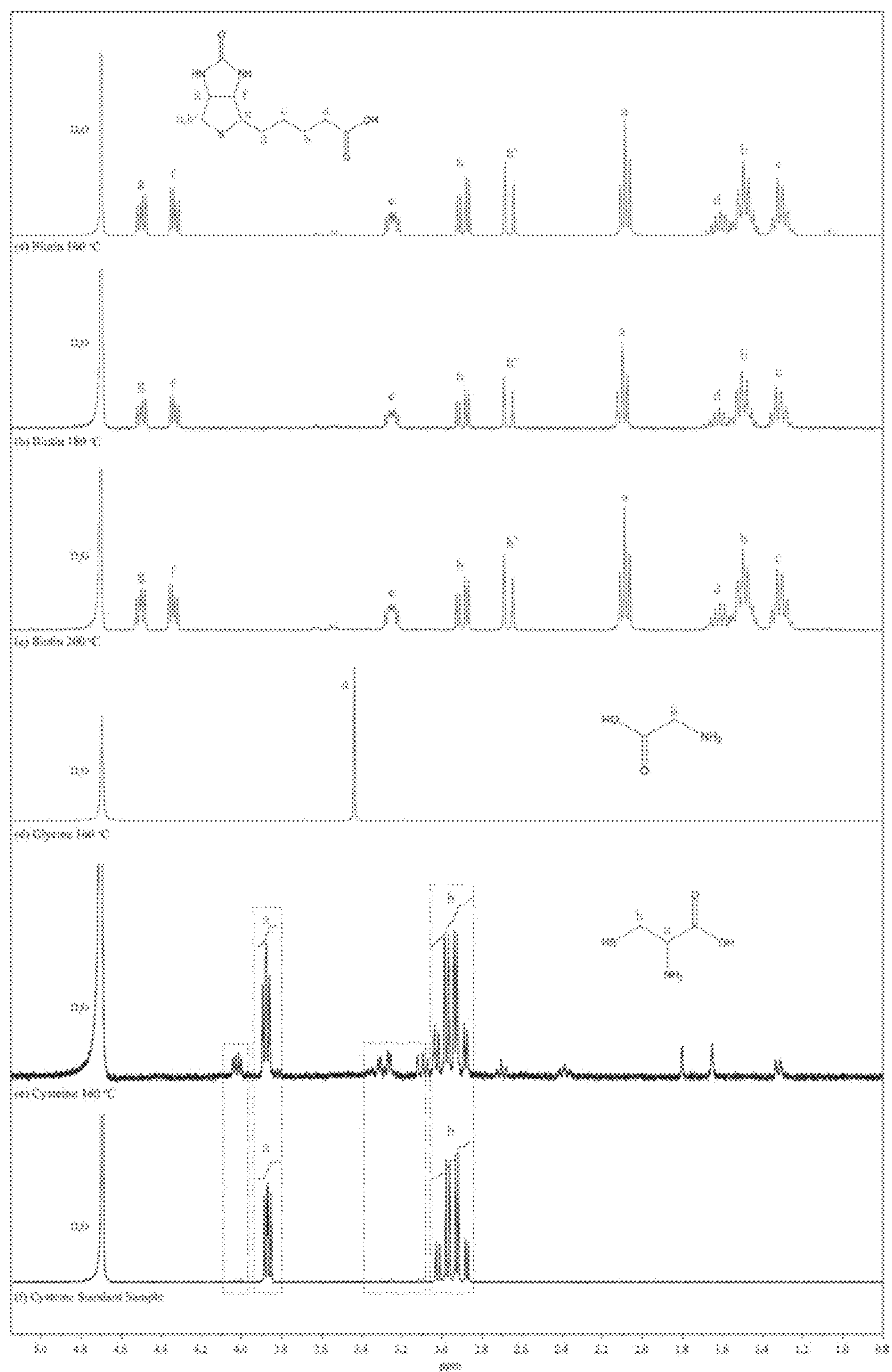
FIG. 5 illustrates a comparison of $^{1}H$ NMR Spectra of different kinds of biomolecules: (a) biotin with solvothermal treatment at 160° C.; (b) biotin with solvothermal treatment at 180° C.; (c) biotin with solvothermal treatment at 200° C.; (d) glycine with solvothermal treatment at 160° C.; (e) cysteine with solvothermal treatment at 160° C.; (f) cysteine without solvothermal treatment.

FIGS. 5*a-c* illustrate a comparison of $^1$H NMR Spectra of biotin molecules with solvothermal treatment at 160° C., 180° C. and 200° C. respectively. FIG. 5*d* illustrates $^1$H NMR Spectra of glycine molecules with solvothermal treatment at 160° C., whereas FIGS. 5*e-f* illustrate cysteine molecules with and without solvothermal treatment at 160° C. All the samples were dissolved in $D_2O$. All of the three biomolecules survived under the ligand exchange conditions, which show that these three kinds of biomolecules are quite stable even when treated under high temperature during solvothermal treatment. Moreover, the nanoparticles modified with these three kinds of biomolecules are ready for biological applications with bioactivity.

It will be appreciated that by prior removal of the original ligands, a wide variety of molecules can be attached to the nanoparticles through a unified solvothermal process. Removal of oleate ligands and attachment of new ligands being conducted in separate operations is beneficial for reliable attachment of different ligands at mild and consistent experimental conditions. In addition, this invention eliminates the inconvenience associated with direct ligand exchange reactions that require complicated equipment setup and stringent control over experimental variables. At the same time, the solvothermal treatment ensures firm bonding between the nanoparticles and the ligands, leading to good water dispersibility and high stability of the nanoparticles. Furthermore, functional biomolecules such as biotin, cysteine, and glycine can be directly attached to the nanoparticles with preserved bioactivities. This technique can be readily extended to other ligand and nanoparticle systems for applications ranging from biological imaging to lighting and solar cells.

It will be appreciated by persons skilled in the art that numerous variations and/or modifications may be made to the present invention as shown in the specific embodiments without departing from the spirit or scope of the invention as broadly described. The present embodiments are, therefore, to be considered in all respects as illustrative and not restrictive.

It will also be appreciated by persons skilled in the art that the present invention may also include further additional modifications made to the method which does not affect the overall functioning of the method.

Any reference to prior art contained herein is not to be taken as an admission that the information is common general knowledge, unless otherwise indicated. It is to be understood that, if any prior art information is referred to herein, such reference does not constitute an admission that the information forms a part of the common general knowledge in the art, any other country.

The invention claimed is:

1. A two-step method for surface modification of lanthanide-doped nanoparticles comprising the steps of:

(a) removing oleate and/or oleylamine ligands coated on the surface of the lanthanide-doped nanoparticles with hydrochloric acid to form a mixture containing ligand-free lanthanide-doped nanoparticles;

(b) as a separate step from step (a), immobilization of new ligands onto the ligand-free lanthanide-doped nanoparticles to form modified lanthanide-doped nanoparticles with new ligands thereon, by:

(b1) mixing a solution of new ligands of which the pH is adjusted to pH 8 by sodium hydroxide with the mixture containing the ligand-free lanthanide-doped nanoparticles to form preliminary modified lanthanide-doped nanoparticles prior to a solvothermal treatment of the preliminary modified lanthanide-doped nanoparticles, wherein the preliminary modified lanthanide-doped nanoparticles comprise weakly adsorbed new ligands; and (b2) solvothermally treating the preliminary modified lanthanide-doped nanoparticles to convert the preliminary modified lanthanide-doped nanoparticles to the modified lanthanide-doped nanoparticles with firmly bonded new ligands thereon;

wherein the new ligands comprise any one of poly(acrylic acid), polyethylenimine, polyvinylpyrrolidone, cysteine, glycine, citric acid, biotin, or aminoethyl phosphate; and wherein the solvothermal treatment comprises maintaining a temperature gradient ranging from 160° C. to 200° C. to minimize ligand degradation.

2. The method according to claim 1 wherein the hydrochloric acid has a concentration of about 0.1M.

3. The method according to claim 1 wherein the solution of new ligands is added to the mixture containing the ligand-free nanoparticles after the pH of the mixture is adjusted to pH 8.

4. The method according to claim 1 wherein the new ligands are provided in an excess compared to the ligand-free lanthanide-doped nanoparticles.

5. The method according to claim 1 wherein the mixture of new ligands and the ligand-free lanthanide-doped nanoparticles is stirred for at least two hours.

6. The method according to claim 1 wherein water is substantially removed from the mixture.

7. The method according to claim 6 wherein water is removed by dehydrating the mixture.

8. The method according to claim 1 wherein diethylene glycol is added as a solvothermal solvent for use in solvothermal treatment.

9. The method according to claim 8 wherein the solvothermal treatment comprises heating the solution in an autoclave for at least two hours.

10. The method according to claim 8 wherein the resulting solution is centrifuged.

11. The method according to claim 10 wherein the supernatant di ethylene glycol is removed.

12. The method according to claim 11 wherein the pellet of nanoparticles is washed with a mixture of water and ethanol.

* * * * *